United States Patent
Fletcher et al.

(10) Patent No.: US 6,820,463 B2
(45) Date of Patent: Nov. 23, 2004

(54) APPARATUS AND METHOD OF TESTING PRESSURISED CONTAINERS BY NON-INVASIVE MEANS

(75) Inventors: Ian Fletcher, Loughborough (GB); Stephen Metcalf, Loughborough (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/476,900

(22) PCT Filed: May 8, 2002

(86) PCT No.: PCT/SE02/00903
§ 371 (c)(1),
(2), (4) Date: Nov. 4, 2003

(87) PCT Pub. No.: WO02/090940
PCT Pub. Date: Nov. 14, 2002

(65) Prior Publication Data
US 2004/0134257 A1 Jul. 15, 2004

(30) Foreign Application Priority Data
May 9, 2001 (SE) .............................. 0101597

(51) Int. Cl.⁷ ............................................... G01M 3/02
(52) U.S. Cl. ............................................... 73/37; 73/52
(58) Field of Search ....................................... 73/37, 52

(56) References Cited

U.S. PATENT DOCUMENTS

| | | | | |
|---|---|---|---|---|
| 3,830,632 A | * | 8/1974 | Guzay | 422/120 |
| 4,991,751 A | * | 2/1991 | Naku | 222/402.13 |
| 5,313,955 A | * | 5/1994 | Rodder | 600/538 |
| 6,006,745 A | * | 12/1999 | Marecki | 128/200.23 |
| 6,030,682 A | * | 2/2000 | Marecki | 428/66.4 |
| 6,358,058 B1 | * | 3/2002 | Strupat et al. | 434/262 |
| 6,413,496 B1 | * | 7/2002 | Goodman et al. | 424/45 |

FOREIGN PATENT DOCUMENTS

| | | |
|---|---|---|
| GB | 1 597 904 | 9/1981 |
| SE | 428 837 | 10/1976 |
| WO | WO 99/54210 | 10/1999 |
| WO | WO 99/54211 | 10/1999 |
| WO | WO 99/54212 | 10/1999 |

* cited by examiner

*Primary Examiner*—Hezron Williams
*Assistant Examiner*—Rodney Frank
(74) *Attorney, Agent, or Firm*—Fish & Richardson P.C.

(57) ABSTRACT

The invention relates to testing apparatus (1) for testing a container (2) of a suspension of a substance (3). The substance may in particular, but not solely, comprise a pharmaceutical substance. The substance (3) is suspended in a propellant (4), which is under pressure. The container (2) itself comprises a body (5), which defines a chamber and has a valve stem (6), which extends from a head of the body. A metering chamber is selectively communicable, by means of the valve stem, with the atmosphere and the chamber (7). The valve stem providing via a L-shaped conduit, which extends between the free end and the side wall thereof the outlet of the container (2) through which metered doses of the substance are released from the container (2). The testing apparatus (1) includes a gallery (8) for communicating, in use, in a fluid-tight manner with the said valve stem and actuating means, in use, actuating the valve stem so as to discharge a metered dose of substance and/or propellant into the gallery, repeatedly if necessary, until the pressure within the gallery is substantially equalised with the pressure within the container (2). The testing apparatus further includes pressure-measuring means (9) in communication with said gallery to provide a measurement of the pressure therein and hence the pressure within the container (2).

12 Claims, 3 Drawing Sheets

APPARATUS AND METHOD OF TESTING PRESSURISED CONTAINERS BY NON-INVASIVE MEANS

Figure 1:
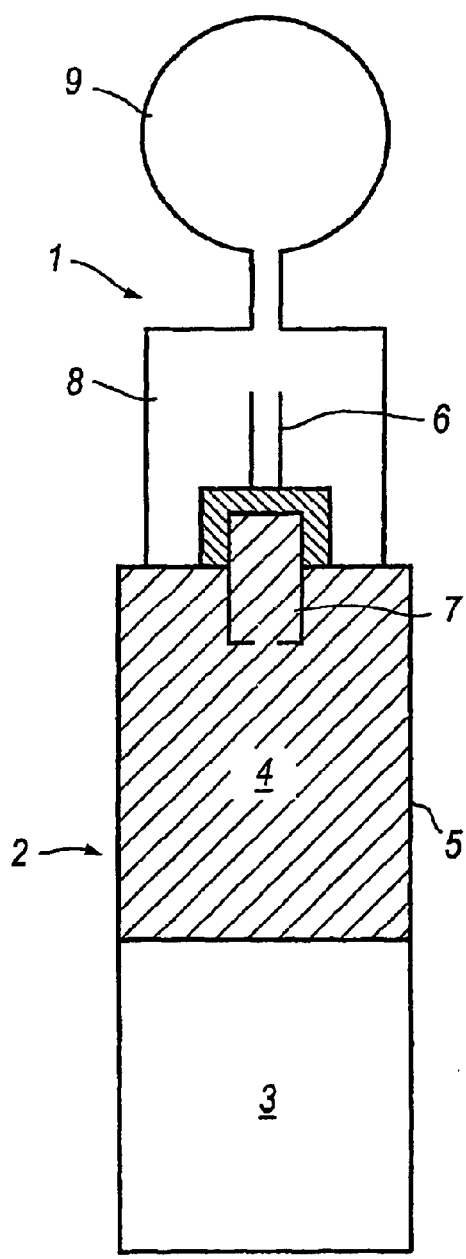

This invention relates to the testing of pressurised containers, such as, but not solely, pharmaceutical pressurised metered dose inhalers (pMDI) and in particular to non invasive methods and apparatus for testing or measuring the internal vapour pressure of such containers.

BACKGROUND OF THE INVENTION

Pressurised containers are used in a variety of fields, they may, for example provide a source of substance for dispensing. An example of such a container is used in the medical field where it may provide a supply of pharmaceutical substance for an inhaler, in particular a metered dose inhaler. It will be appreciated that there are a variety of other uses that such containers can be put to.

Containers for holding a suspension or solution of a pharmaceutical substance in a propellant under pressure are well known. One such known container comprises a body which defines a chamber, a valve stem which extends from a head of the body and a metering chamber which is selectively communicable by the valve stem with the atmosphere and the chamber; the valve stem providing, via an L-shaped conduit which extends between the free end and the side wall thereof, the outlet of the container through which metered doses of propellant containing pharmaceutical substance are delivered. The valve stem is axially displaceable between a first, extended position in which the metering chamber, and hence the container, is closed to the atmosphere since the L-shaped conduit is disposed wholly outside the metering chamber, and a second, depressed position, in which the metering chamber is in open communication with the outlet provided by the L-shaped conduit in the valve stem and through which a metered dose of propellant containing pharmaceutical substance is delivered. The container is filled with the valve stem in the depressed position, with the propellant containing pharmaceutical substance being forced downwardly through the L-shaped conduit in the valve stem, the metering chamber and into the chamber defined by the body of the container.

In the field of metered dose containers it is necessary to test or check the contents of such containers. Testing provides information on the level of pharmaceutical substance in the container and also the level of propellant. The level of pharmaceutical substance is important as it relates to the number of doses that the container can dispense. In some cases the level of pharmaceutical substance is set by regulation and the level in the container must fall within a narrow band.

One test performed on such containers is the measurement of the internal vapour pressure. This may be required for a number of reasons, for example, to ensure that air has been removed from the container in the purging stage of production, to ensure that the ratio of the blended propellants to the pharmaceutical substance is correct or to ensure that additional air has not been added to the container during production.

There are a variety of methods of filling such containers, which are known, for example European Patents having publication numbers EP1084059, EP1073587 and EP1080014, However methods and apparatus for testing the internal vapour pressure of a metering container so filled have tended to be unrefined. Methods, which exist, consist of invasive techniques. For example, one known method involves piercing the base of an inverted container and connected the vapour in the headspace to a pressure gauge. After the measurement is complete the contents of the pMDI are vented to the atmosphere. However propellants generally used such as CFCs are considered harmful both to any operators which may be near by and to the general environment. In this method the full contents of the container must be vented and therefor wasted. As the test is destructive, lower yields result from performing the test during manufacture. One known technique of performing this method involves an operator simply piercing the container by means of a sharp object such as a spike. There are obviously other disadvantages of such a method such the risk of injury to the operator.

One further disadvantage of the method described above is that evaporation of the liquid propellant occurs when the device is vented thus leading to localised cooling of the apparatus, this affects the pressure reading of subsequent pMDIs.

There therefor exists a need for a method and apparatus for testing the internal pressure of a container by non invasive means.

Herein non invasive may be said to be defined as not involving the introduction of instruments or devices into the container being tested, in particular not involving the piercing of the container wall.

SUMMARY OF THE INVENTION

The present invention in at least one preferred aspect aims to provide an improved testing method or testing apparatus, which at least partially overcomes the above-mentioned problems.

The present invention also aims to provide a method and apparatus which are adapted to test or measure the internal pressure of a container reduces the amount of propellant alone or propellant containing pharmaceutical substance released to the atmosphere.

In a preferred form the present invention consists of apparatus for providing an indication of the level of contents of a pressurised metered dose container.

According to a first aspect of the present invention there is provided testing apparatus for testing a container containing a suspension or solution of a substance, in particular, but not solely, a pharmaceutical substance, in a propellant under pressure, said container comprising a body which defines a chamber, a valve stem which extends from a head of the body and a metering chamber which is selectively communicable by the valve stem with the atmosphere and the chamber; the valve stem providing; via an L-shaped conduit which extends between the free end and the side wall thereof, the outlet of the container through which metered doses of the substance are released from said container, said testing apparatus characterised in that it comprises: a gallery for communicating, in use, in a fluid-tight manner with said valve stem; actuating means, in use, actuating said valve stem so as to discharge a metered dose of substance into said gallery, repeatably, if necessary, until the pressure within the gallery is substantially equalised with the pressure within the container; pressure measuring means in communication, in use, with said gallery and providing a measurement of the pressure therein.

Preferably the actuating apparatus comprises a manually operated handle bearing against said valve stem.

Preferably the actuating means comprises a cam which in one position directly or indirectly actuates the valve stem.

Preferably the actuating means comprises electromechanicaly operable means which preferably automatically actuates the valve stem.

Preferably the pressuring measuring means comprises a pressure cell.

Preferably the pressure measuring means comprises means which provides a feedback into the manufacturing process of said containers providing adjustment of the process so that a pre-set limit of pressure within the containers is maintained.

According to another aspect of the present invention there is provided a method of testing a container containing a suspension or solution of a substance, in particular, but not solely, a pharmaceutical substance, in a propellant under pressure, said container comprising a body which defines a chamber, a valve stem which extends from a head of the body and a metering chamber which is selectively communicable by the valve stem with the atmosphere and the chamber; the valve stem providing, via an L-shaped conduit which extends between the free end and the side wall thereof, the outlet of the container through which metered doses of the substance are released from said container, said method characterised in that it comprises the steps of:

providing a gallery in fluid-tight communication with said valve stem;

actuating said valve stem so as to discharge a metered dose of substance into said gallery, repeatably, if necessary, until the pressure within the gallery is substantially equalised with the pressure within the container;

measuring the pressure within said gallery.

Preferably the actuating apparatus comprises a manually operated handle bearing against said valve stem.

Preferably the actuating means comprises a cam which in one position directly or indirectly actuates the valve stem.

Preferably the actuating means comprises electromechanicaly operable means which preferably automatically actuates the valve stem.

Preferably the pressuring measuring means comprises a pressure cell.

Preferably the pressure measuring means comprises means which provides a feedback into the manufacturing process of said containers providing adjustment of the process so that a pre-set limit of pressure within the containers is maintained.

BRIEF DESCRIPTION OF THE INVENTION

Figure 2:
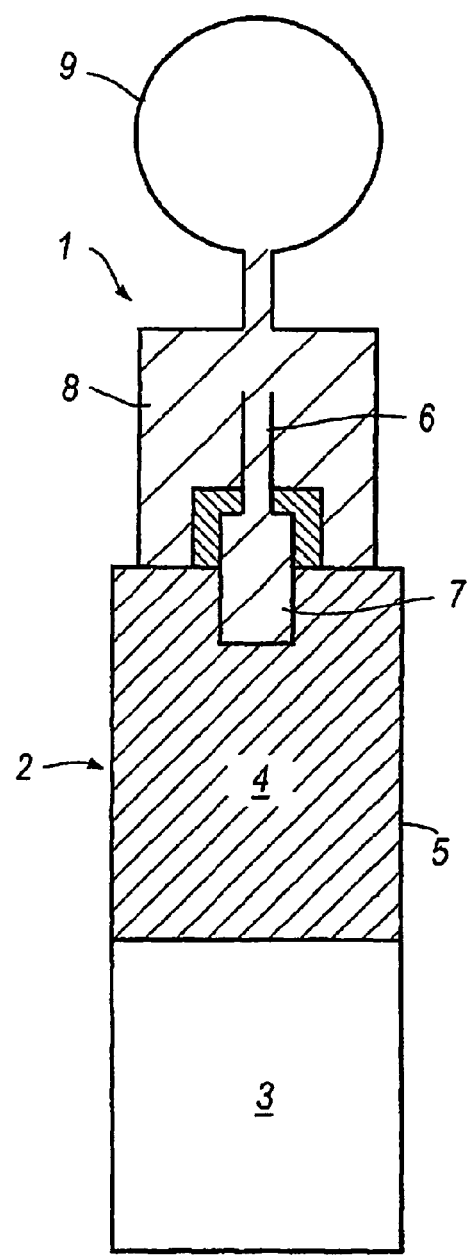
Figure 3:
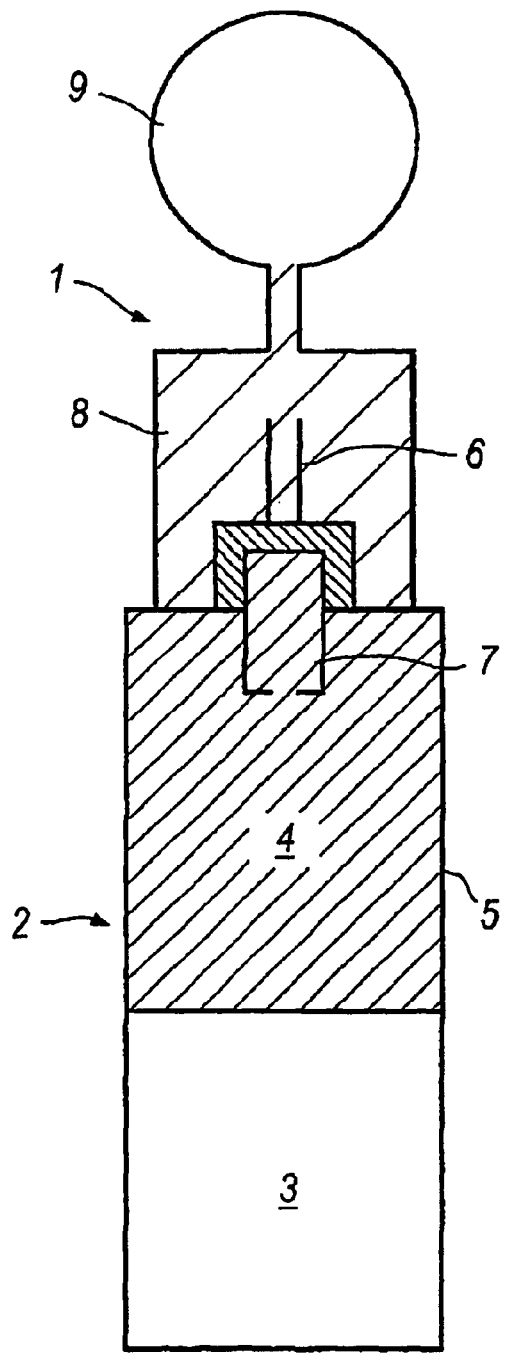
Figure 4:
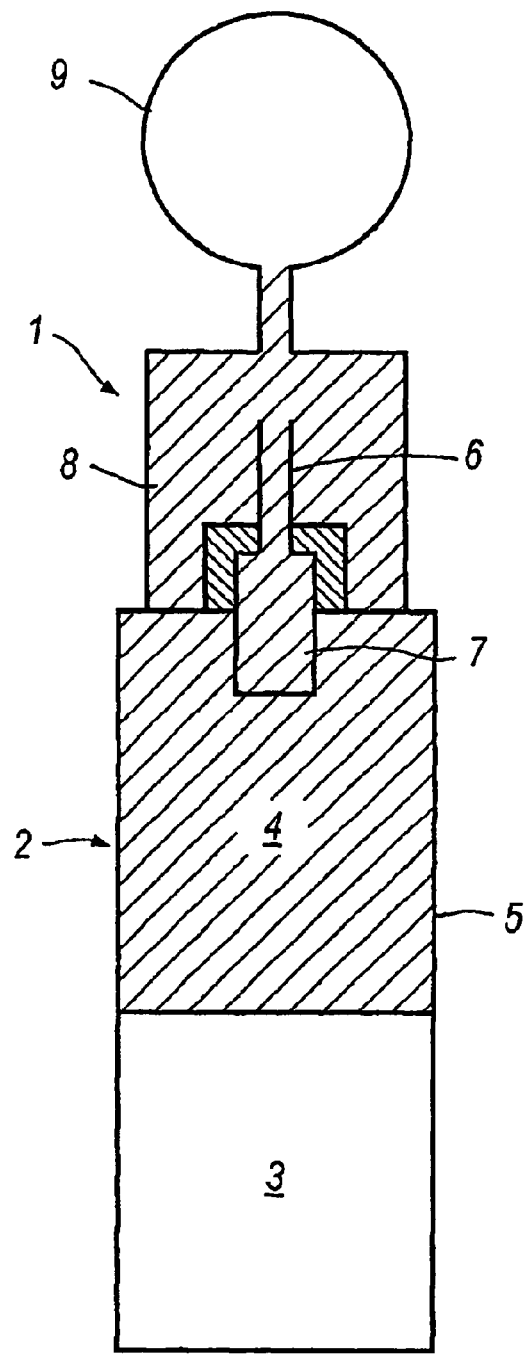
Figure 5:
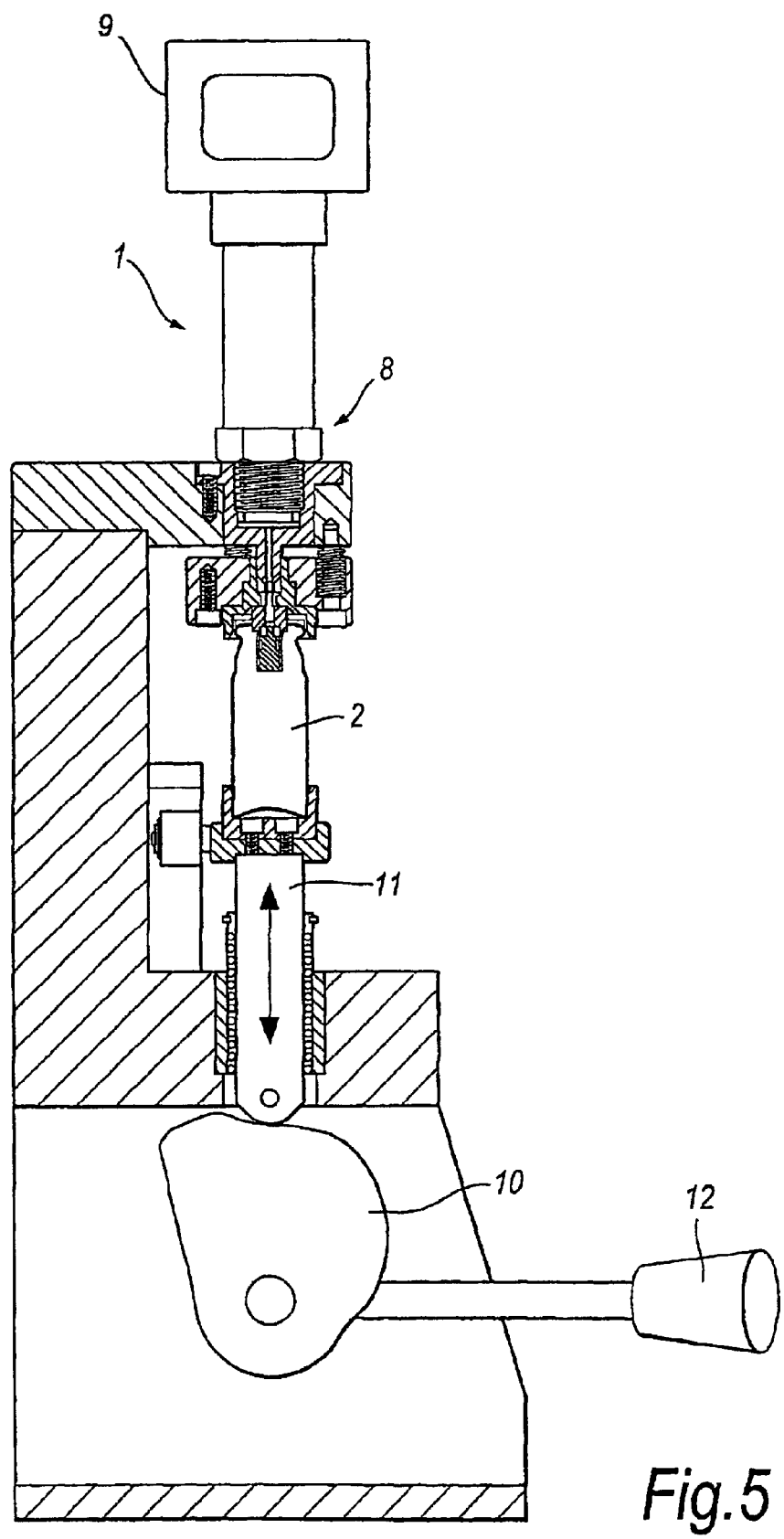

A preferred embodiment of the present invention will now be described hereinbelow by way of example only with reference to the accompanying drawings, in which:

FIG. 1 shows a schematic view of apparatus according to an embodiment of the present invention wherein the apparatus is in the starting position, FIG. 2 shows a schematic view of apparatus according to an embodiment of the present invention wherein the apparatus is actuating the pMDI value, FIG. 3 shows a schematic view of apparatus according to an embodiment of the present invention wherein the metering chamber is refilling with vapour from the container, FIG. 4 shows a schematic view of apparatus according to an embodiment of the present invention wherein the pressure within the pressure cell is at equilibrium with the vapour in the pMDI thus enabling pressure measurement to occur, and FIG. 5 shows a preferred form of the invention which uses a manually actuated 12 cam 10 to actuate the valve of the canister 2, the cam acts via a force transmitting element 11.

DESCRIPTION OF THE PREFERRED EMBODIMENTS

The metering valve 6, 7 of a MDI 2 is designed to allow a set volume of pharmaceutical active substance 3 to be dispensed upon actuation. This volume is typically 50 μl, but, of course, may vary. The metering chamber 6, 7 within the valve defines this fixed volume. When the valve is at rest, the metering chamber is open to the contents of the pMDI. When the valve is actuated, this path closes, and another channel opens to the atmosphere. At rest the metering chamber fills with the contents of the pMDI (the liquid pharmaceutically active substance), which is then discharged when the pMDI is actuated.

Embodiments of the present invention utilise this mechanism to measure the vapour pressure within the pMDI. If the pMDI is held upright, the metering chamber will fill with vapour from the headspace. When the valve is actuated 6, 7, this vapour will be discharged via the valve stem. By enclosing the top of the valve in a pressure cell, the discharged vapour can be contained. By repeatedly actuating the metering valve into this cell, the pressure will reach equilibrium with the vapour within the pMDI container 2. Coupling a pressure gauge 9 or transducer measures this to the cell.

One embodiment of the present invention uses a pressure gauge 9, which comprises a standard gauge for providing a readout of the pressure within an enclosed volume. Such devices range from simple mechanical means to electromechanical and purely electronic devices.

In an embodiment of the present invention the pressure gauge 9 simply provides a read out of the pressure which can be noted by an operator and any necessary action or adjustment of the process taken. In other embodiments of the invention there may be a feed back loop from the pressure gauge 9 so that the adjustment of the process may take place automatically. In other embodiments of the invention the pressure gauge 9 may simply be linked to a monitoring system whereby any discrepancy in the pressure measured is reported and noted.

The method of measuring the vapour pressure of a pMDI canister or container 2 according to one embodiment of the present invention occurs as one step in the process of producing a filled pMDI container 2. The process will now be briefly outlined. Cans and valves are produced and assembled into a container 2. The valve 6, 7 is placed in or on the can. At this stage the assembled containers are purged so as to ensure that they contain only propellant and not a mixture of air and propellant. Air should be purged from the container 2 as it can have an affect on the pharmaceutically active substance. It may for example include moisture and therefore reduce the shelf life of the product. Following purging the assembled can and valve is crimped to join the valve to the can thus completing the container 2. The crimped container 2 is then pressure filled through the valve with the product suspension preparation, that is the pharmaceutically active substance. After the container 2 is filled it may be subjected to a series of tests, for example to check the weight of the container 2.

The method of measuring the vapour pressure of the filled container 2 according to an embodiment of the present invention involves the following steps. Bringing a pressure cell 9 into fluid communication with the metering valve of the pMDI 2 to be tested. The pressure cell 9 includes means for providing a measurement of the pressure contained therein. The metering valve of the pMDI 2 is then actuated. The actuation may be preformed by an operator but in the preferred embodiment of the invention occurs automaticaly. The pressure in the pressure cell is montored and the actuation of the metering valve 6, 7 is repeated until the pressure in the pressure cell is stable. At this time the pressure in the pressure cell is equal to the pressure in the container. This is because the metering valve, that is the valve stem and the metering chamber 6,7 has acted as a shuttle valve transferring contents of the container to the pressure cell until the pressure within the two are equal. The pressure in the pressure cell or gallery 8 can then be measured which will be equal to the pressure within the container 2.

Improvements to the system can be brought about by the use of smaller galleries 8 within the pressure measurement cell 9 or by automating the system to increase throughput.

The possibility exists to extend the testing from an in-process test to a 100% test of all units to ensure the correct internal pressure. This would be the only way of ensuring that a failure of the purger mechanism does not result in the release from the production run of pMDIs 2 that are unpurged. Such an embodiment of the present invention would be advantageous when used in conjunction with the feedback system referred to above.

The form of the invention shown in FIG. 5 uses a cam 10 which acts on the base of the canister 2 by means of a force transmitting element 11. The cam is itself actuated by means of a handle 12, which is manually rotated in order to cause the cam 10 to actuate the valve of the canister 2.

It should be noted that the present invention does release a small amount of propellant from the pMDI or container 2. However the amount released is simply the amount contained in the gallery and is small in comparison with the amount in the entire container 2 and is significantly less than that released in the prior art methods. It should also be noted that it is mainly propellant 3 that is released and not, as in prior art methods, propellant and pharmaceutically active substance.

Finally, it will be understood by a person skilled in the art that the present invention has been described in at least one preferred embodiment and can be modified in many different ways without departing from the scope of the invention as defined in the appended claims.

What is claimed is:

1. Testing apparatus (1) for testing a container (2) containing a suspension or solution of a substance (3), in particular, but not solely, a pharmaceutical substance, in a propellant (4) under pressure, said container comprising a body (5) which defines a chamber, a valve stem (6) which extends from a head of the body and a metering chamber (7) which is selectively communicable by the valve stem (6) with the atmosphere and the chamber (7); the valve stem providing, via an L-shaped conduit which extends between the free end and the side wall thereof, the outlet of the container (2) through which metered doses of the substance are released from said container (2), said testing apparatus (1) characterised in that it comprises: a gallery (8) for communicating, in use, in a fluid-tight manner with said valve stem; actuating means, in use, actuating said valve stem so as to discharge a metered dose of substance (3) and/or propellant (4) into said gallery (8), repeatably if necessary, until the pressure within the gallery (8) is substantially equalised with the pressure within the container (2); pressure measuring means (9) in communication, in use, with said gallery (8) and providing a measurement of the pressure therein.

2. Testing apparatus as claimed in claim 1 wherein the actuating apparatus comprises a manually operated handle against said valve stem (6).

3. Testing apparatus as claimed in claim 1 wherein the actuating means comprises a cam which in one position directly or indirectly actuates the valve stem (6).

4. Testing apparatus (1) as claimed in claim 1 wherein the actuating means comprises electromechanical operable means, which preferably automatically actuates the valve stem (6).

5. Testing apparatus as claimed in claim 1 wherein the pressuring measuring means (9) comprises a pressure cell (9).

6. Testing apparatus as claimed in claim 1 wherein the pressure measuring means (9) comprises means which provides a feedback into the manufacturing process of said containers providing adjustment of the process so that a pre-set limit of pressure within the containers (2) is maintained.

7. A method of testing a container (2) containing a suspension or solution of a substance (3), in particular, but not solely, a pharmaceutical substance, in a propellant (4) under pressure, said container (2) comprising a body which defines a chamber (7), a valve stem (6) which extends from a head of the body (7) and a metering chamber which is selectively communicable by the valve stem (6) with the atmosphere and the chamber; the valve stem (6) providing, via an L-shaped conduit which extends between the free and the side wall thereof, the outlet of the container (2) through which metered doses of the substance (3) are, released from said container (2), said method characterised in that it comprises the steps of: providing a gallery (8) in fluid-tight communication with said valve stem (2); actuating said valve stem (2) so as to discharge a metered dose of substance (3) and/or propellant (4) into said gallery (8), repeatably, if necessary, until the pressure within the gallery (8) is substantially equalised with the pressure within the container (2); measuring the pressure within said gallery (8).

8. A method of testing as claimed in claim 7 wherein the actuating apparatus comprises a manually operated handle bearing against said valve stem (2).

9. A method of testing as claimed in claim 7 wherein the actuating means comprises a cam which in one position directly or indirectly actuates the valve stem (2).

10. A method of testing as claimed in claim 7 wherein the actuating means comprises electromechanically operable means, which preferably automatically actuates the valve stem (2).

11. A method of testing as claimed in claim 7 wherein the pressuring measuring (9) means comprises a pressure cell.

12. A method of testing as claimed in claim 7 wherein the pressure measuring means (9) comprises means which provides a feedback into the manufacturing process of said containers providing adjustment of the process so that a pre-set limit of pressure within the containers (2) is maintained.

* * * * *